US00PP28524P3

(12) United States Plant Patent
Holtmaat

(10) Patent No.: US PP28,524 P3
(45) Date of Patent: Oct. 10, 2017

(54) ***ECHINACEA* PLANT NAMED 'POST301'**

(50) Latin Name: *Echinacea hybrida*
Varietal Denomination: POST301

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 57 days.

(21) Appl. No.: 14/756,657

(22) Filed: Sep. 29, 2015

(65) Prior Publication Data

US 2017/0094879 P1 Mar. 30, 2017

(51) Int. Cl.
*A01H 5/02* (2006.01)

(52) U.S. Cl.
USPC ..... Plt./428

(58) Field of Classification Search
USPC ..... Plt./428
See application file for complete search history.

(56) References Cited

PUBLICATIONS

AB Cultivars Breeding for Better Gardens *Echinacea* Postman, retrieved on Jan. 19, 2017, retrieved from the Internet at<http://www.ab-cultivars.com/en/assortment/echinacea-postman/> one page.*

* cited by examiner

*Primary Examiner* — June Hwu
(74) *Attorney, Agent, or Firm* — C. A. Whealy

(57) ABSTRACT

A new and distinct cultivar of *Echinacea* plant named 'Post301', characterized by its upright and relatively compact plant habit; moderately vigorous growth habit; freely branching habit; strong flowering stems; numerous large single-type inflorescences with red-colored ray florets and dark red-colored receptacle spines; and good garden performance.

2 Drawing Sheets

Botanical designation: *Echinacea hybrida.*
Cultivar denomination: 'POST301'.

BACKGROUND OF THE INVENTION

The present invention relates to a new and distinct cultivar of *Echinacea* plant, botanically known as *Echinacea hybrida*, and hereinafter referred to by the name 'Post301'.

The new *Echinacea* plant is a product of a planned breeding program conducted by the Inventor in Zuidwolde, The Netherlands. The objective of the breeding program is to develop new freely flowering and relatively compact *Echinacea* plants with unique and attractive ray floret coloration.

The new *Echinacea* plant originated from a cross-pollination in June, 2012 in Zuidwolde, The Netherlands of a proprietary selection of *Echinacea hybrida* identified as code number 651-01, not patented, as the female, or seed, parent with *Echinacea hybrida* 'Purple Emperor', disclosed in U.S. Plant Pat. No. 24,459, as the male, or pollen, parent. The new *Echinacea* plant was discovered and selected by the Inventor as a single flowering plant from within the progeny of the stated cross-pollination grown in a controlled greenhouse environment in Zuidwolde, The Netherlands in July, 2014.

Asexual reproduction of the new *Echinacea* plant by in vitro meristem culture in a controlled environment in Zuidwolde, The Netherlands since December, 2014 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Post301'. These characteristics in combination distinguish 'Post301' as a new and distinct *Echinacea* plant:

1. Upright and relatively compact plant habit.
2. Moderately vigorous growth habit.
3. Freely branching habit.
4. Strong flowering stems.
5. Numerous large single-type inflorescences with red-colored ray florets and dark red-colored receptacle spines.
6. Good garden performance.

Plants of the new *Echinacea* can be compared to plants of the female parent selection. Plants of the new *Echinacea* differ primarily from plants of the female parent selection in the following characteristics:

1. Plants of the new *Echinacea* are shorter than plants of the female parent selection.
2. Plants of the new *Echinacea* are not as freely branching as plants of the female parent selection.
3. Plants of the new *Echinacea* have larger inflorescences than plants of the female parent selection.

Plants of the new *Echinacea* can be compared to plants of the male parent, 'Purple Emperor'. Plants of the new *Echinacea* differ primarily from plants of 'Purple Emperor' in the following characteristics:

1. Plants of the new *Echinacea* are shorter than plants of 'Purple Emperor'.
2. Plants of the new *Echinacea* are not as freely branching as plants of 'Purple Emperor'.
3. Plants of the new *Echinacea* and 'Purple Emperor' differ in ray floret color as ray florets of plants of 'Purple Emperor' are purple pink in color.

Plants of the new *Echinacea* can be compared to plants of *Echinacea* spp. 'Tomato Soup', disclosed in U.S. Plant Pat. No. 19,427. In side-by-side comparisons conducted in Zuidwolde, The Netherlands, plants of the new *Echinacea* differed primarily from plants of 'Tomato Soup' in the following characteristics:

1. Plants of the new *Echinacea* were shorter than plants of 'Tomato Soup'.
2. Plants of the new *Echinacea* were more freely branching than plants of 'Tomato Soup'.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet is a side perspective view of a typical flowering plant of 'Post301' grown in ground beds in an outdoor nursery and placed in a 17.5 cm by 22 cm container for the photograph.

The photographs on the second sheet are close-up views of a typical inflorescence (upper photograph) and the upper surface of typical leaves (lower photograph) of 'Post301'.

DETAILED BOTANICAL DESCRIPTION

The aforementioned photographs and following observations and measurements describe plants grown during the summer in ground beds in an outdoor nursery in Zuidwolde, The Netherlands and under cultural practices typically used in commercial *Echinacea* production. During the production of the plants, day temperatures ranged from 18° C. to 32° C. and night temperatures ranged from 8° C. to 20° C. Plants were eight months old when the photographs and description were taken. In the following description, color references are made to The Royal Horticultural Society Colour Chart, 2007 Edition, except where general terms of ordinary dictionary significance are used.

Botanical classification: *Echinacea hybrida* 'Post301'.

Parentage:

*Female parent*.—Proprietary selection of *Echinacea hybrida* identified as code number 651-01, not patented.

*Male parent*.—*Echinacea hybrida* 'Purple Emperor', disclosed in U.S. Plant Pat. No. 24,459.

Propagation:

*Type*.—By in vitro meristem culture.

*Time to initiate roots, summer*.—About one week at temperatures about 25° C.

*Time to produce a rooted young plant, summer*.—About five weeks at temperatures about 21° C.

*Root description*.—Fine, fibrous; typically pale cream in color, actual color of the roots is dependent on substrate composition, water quality, fertilizer type and formulation, substrate temperature and physiological age of roots.

*Rooting habit*.—Freely branching; medium density.

Plant description:

*Plant form and growth habit*.—Herbaceous perennial; upright and relatively compact plant habit, broad inverted triangle; freely branching habit with about six primary branches developing per plant; moderately vigorous growth habit.

*Plant height*.—About 60 cm.

*Plant diameter or spread*.—About 60 cm.

*Lateral branches*.—Length: About 36.2 cm. Diameter: About 7 mm. Internode length: About 5.5 cm. Aspect: Erect to about 10° from vertical. Strength: Strong. Texture: Smooth, glabrous. Color: Close to 144B to 144C; distally, tinged with close to 184B.

Leaf description:

*Basal leaves*.—Arrangement: Alternate, simple. Length: About 19.3 cm. Width: About 4.7 cm. Shape: Narrowly ovate. Apex: Acute. Base: Attenuate. Margin: Shallowly dentate; slightly undulate. Texture and luster, upper and lower surfaces: Moderately pubescent, strigose, rough; moderately glossy. Venation pattern: Pinnate. Color: Developing leaves, upper surface: Close to between 141A and 143A. Developing leaves, lower surface: Close to between 137C and 138A. Fully expanded leaves, upper surface: Close to between 137A and NN137D; venation, close to 146C to 146D. Fully expanded leaves, lower surface: Close to 137B; venation, close to 145A to 145B. Petioles, basal leaves: Length: About 8.4 cm. Diameter: About 4 mm. Height: About 5 mm. Strength: Strong, flexible. Texture and luster, upper and lower surfaces: Mostly glabrous; margins, sparsely pubescent, strigose; slightly glossy. Color, upper surface: Close to 145D; margins, close to 141B. Color, lower surface: Close to 145A; margins, close to 137A.

*Cauline leaves*.—Arrangement: Alternate, simple. Length: About 8.5 cm. Width: About 1.4 cm. Shape: Narrowly ovate. Apex: Acute. Base: Attenuate. Margin: Shallowly dentate; slightly undulate. Texture and luster, upper and lower surfaces: Moderately pubescent, strigose, rough; moderately glossy. Venation pattern: Pinnate. Color: Developing leaves, upper surface: Close to between 141A and 143A. Developing leaves, lower surface: Close to between 137C and 138A. Fully expanded leaves, upper surface: Close to between 137A and NN137D; venation, close to 146C to 146D. Fully expanded leaves, lower surface: Close to 137B; venation, close to 145A to 145B. Petioles, cauline leaves: Length: About 4 mm. Diameter: About 2 mm. Height: About 3 mm. Strength: Strong, flexible. Texture and luster, upper and lower surfaces: Mostly glabrous; margins, sparsely pubescent, strigose; slightly glossy. Color, upper surface: Close to 145D; margins, close to 141B. Color, lower surface: Close to 145A; margins, close to 137A.

Inflorescence description:

*Appearance*.—Large single-type inflorescences with ray and disc florets arranged on a capitulum; inflorescences positioned upright above the foliar plane on mostly upright and strong peduncles.

*Flowering habit*.—Freely flowering habit with about 25 inflorescences developing per plant during the flowering season.

*Fragrance*.—Moderately fragrant; somewhat acidic, pleasant.

*Time to flower*.—In the garden, plants flower continuously from early July to late September in The Netherlands.

*Inflorescence longevity*.—Inflorescences maintain good substance for about three weeks on the plant; inflorescences persistent.

*Inflorescence buds*.—Height: About 1.7 cm. Diameter: About 3 cm. Shape: Flattened globular. Color: Involucral bracts, close to 137A; ray florets, close to 151C to 151D.

*Inflorescence size*.—Diameter: About 10.2 cm. Depth (height): About 6.2 cm. Disc diameter: About 4.2 cm. Receptacle height: About 1.8 cm. Receptacle diameter: About 1.5 cm. Receptacle color: Close to 155B.

*Ray florets*.—Quantity and arrangement: About 34 arranged in about two whorls at the base of the receptacle. Length: About 5.5 cm. Width: About 1 cm. Shape: Oblanceolate. Apex: Emarginate to praemorse. Base: Cuneate. Margin: Entire. Texture, upper surface: Glabrous; velvety; slightly longitudinally ridged. Texture, lower surface: Glabrous; longitudinally ridged. Luster, upper surface: Matte. Luster, lower surface: Slightly glossy. Aspect: Horizontal to drooping, about 20° from horizontal. Color: When opening, upper surface: Close to N30C to N30D; towards the base, slightly lighter than N34A. When opening, lower surface: Close to between 53D and 180C. Fully opened, upper surface: Close to between 42A and 45A; color becoming closer to 172B and towards the base, close to 185A, with development. Fully opened, lower surface: Close to 48A; color becoming closer to 176B to 176C with development.

*Disc florets*.—Quantity and arrangement: About 400 per inflorescence, spirally at the center. Length: About 1.2 cm. Diameter: About 2 mm. Shape: Tubular; proximally, 15% free, not fused. Apex: Acute. Base: Fused. Margin: Entire. Texture, inner and outer surfaces: Smooth, glabrous. Luster, inner and outer surfaces: Glossy. Color, when opening, inner and outer surfaces: Apex: Close to 53A. Mid-section and base: Close to 144C. Color, fully opened, inner and outer surfaces: Apex: Close to 53A. Mid-section and base: Close to 144C to 144D.

*Receptacle spines*.—Quantity: One per disc floret. Shape: Acicular. Apex: Acute. Base: Attenuate. Texture: Smooth, glabrous. Luster: Glossy. Color: Apex: Close to 53A to darker than 53A. Mid-section: Close to 26D. Base: Close to 144C.

*Involucral bracts*.—Quantity per inflorescence: About 96 arranged in about four whorls. Length: About 1 cm. Width: About 4 mm. Shape: Ovate to narrowly ovate. Apex: Acute. Base: Cuneate. Margin: Entire. Texture, upper surface: Smooth, glabrous. Texture, lower surface: Moderately pubescent. Luster, upper and lower surfaces: Matte. Color, upper surface: Close to N137A. Color, lower surface: Close to 137A.

*Peduncles*.—Length: About 15 cm. Diameter: About 5 mm. Strength: Strong. Aspect: Upright to about 25° from vertical. Texture: Moderately pubescent; strigose. Color: Close to 147C to 147D tinged with close to 181C.

*Reproductive organs*.—Androecium (present on ray and disc florets): Quantity per floret: Five. Filament length: About 5 mm. Filament color: Close to 145D. Anther length: About 4 mm. Anther shape: Narrowly oblong. Anther color: Close to 200A. Pollen amount: Moderate. Pollen color: Close to 17A. Gynoecium (present only on disc florets): Quantity per floret: One. Pistil length: About 8 mm. Stigma shape: Decurrent, unequal. Stigma color: Close to 200A. Style length: About 6 mm. Style color: Close to 145A. Ovary color: Close to 145D. Seeds and fruits: Seed and fruit development have not been observed on plants of the new *Echinacea*.

Disease & pest resistance: Plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'Post301' as illustrated and described.

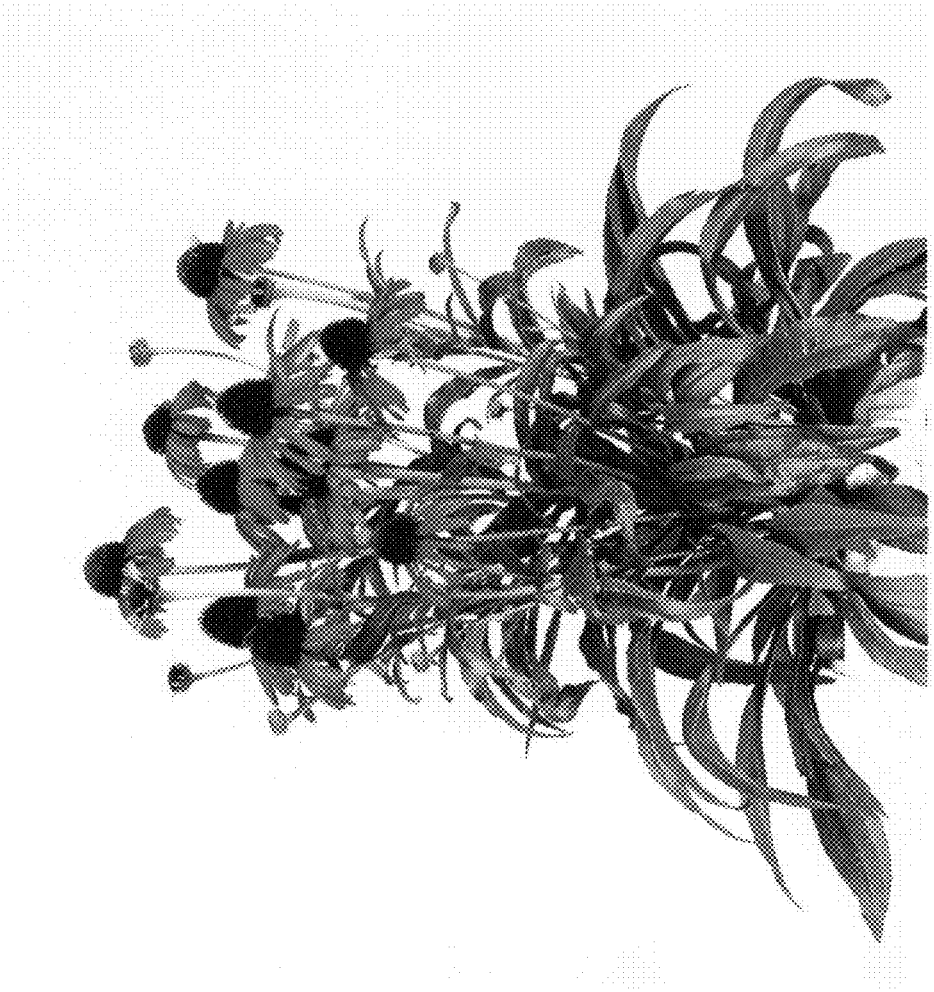

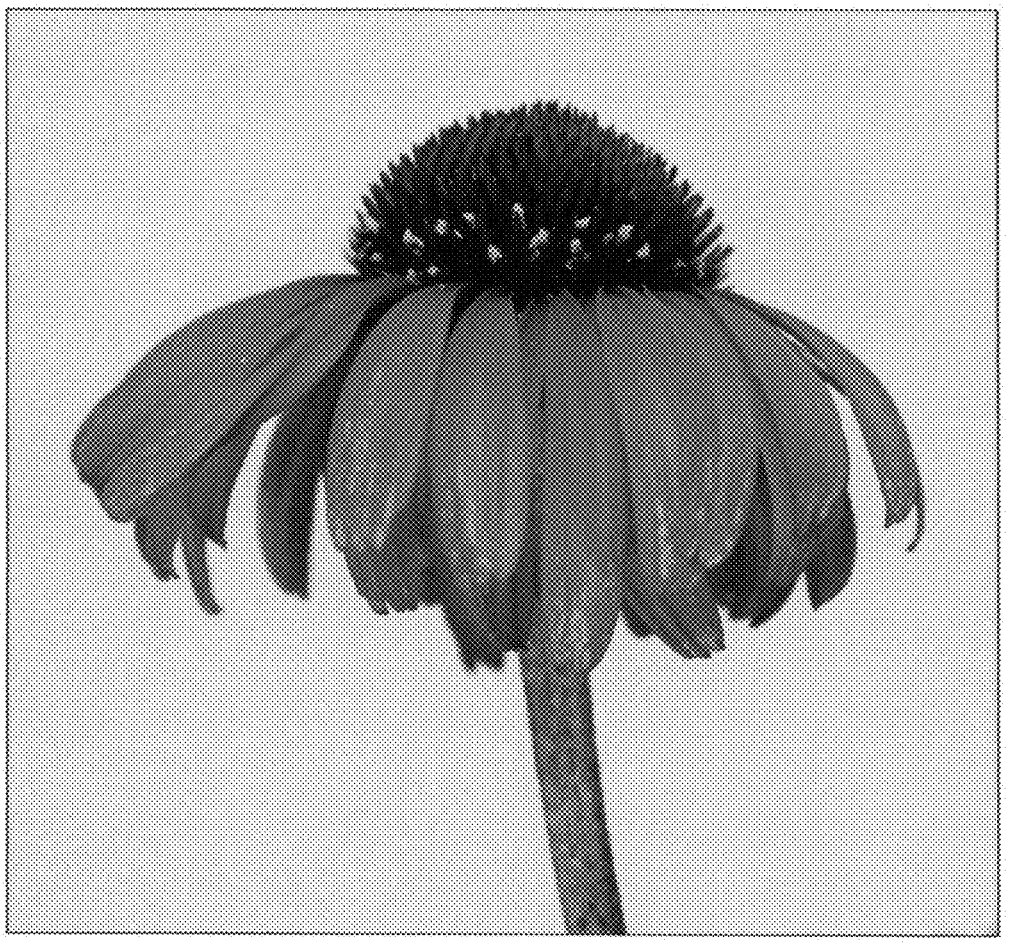
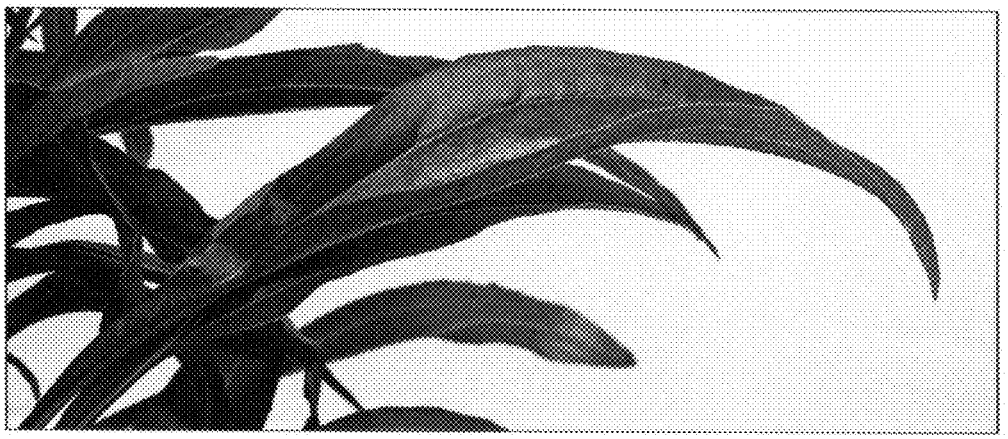

* * * * *